United States Patent [19]

Konyo et al.

[11] Patent Number: 5,130,486
[45] Date of Patent: Jul. 14, 1992

[54] PROCESS FOR ISOMERIZATION OF OXIME ETHERS

[75] Inventors: Naoto Konyo, Osaka; Yukio Yoneyoshi, Aomori; Gohfu Suzukamo, Osaka, all of Japan

[73] Assignee: Sumitomo Chemical Company Limited, Osaka, Japan

[21] Appl. No.: 634,595

[22] Filed: Dec. 27, 1990

[30] Foreign Application Priority Data

Dec. 28, 1989 [JP] Japan .................. 1-343095

[51] Int. Cl.⁵ .................. C07C 249/04; C07C 249/14
[52] U.S. Cl. .................. 564/256; 564/253; 564/258; 564/264; 564/265; 564/268
[58] Field of Search ............. 564/256, 253, 258, 264, 564/265, 268

[56] References Cited

U.S. PATENT DOCUMENTS 4,158,015 6/1979 Paul ..................... 564/256
4,558,043 12/1985 Wenk et al. ............. 514/210

FOREIGN PATENT DOCUMENTS 0009865 4/1980 European Pat. Off. .
62-215558 9/1987 Japan .

OTHER PUBLICATIONS

J. Org. Chem., 20, 1491 (1955).

J. Chem. Soc., Perkin Trans. I, 9, 1691 (1986).

*Primary Examiner*—Richard L. Raymond
*Assistant Examiner*—Shailendra Kumar
*Attorney, Agent, or Firm*—Birch, Stewart, Kolasch & Birch

[57] ABSTRACT

Isomerization of an unsymmetrical ketoxime ether is effected using at least one Lewis acid selected from titanium chloride, titanium bromide, aluminum chloride, aluminum bromide, boron chloride, and boron bromide as isomerizing agents. Examples of the Lewis acid are titanium tetrachloride, titanium trichloride, aluminum trichloride, aluminum tribromide, boron trichloride, and boron tribromide. The ketoxime ether is preferably an anti-isomer or a syn-isomer of a compound represented by the formula (I) or a mixture of the anti-isomer and the syn-isomer:

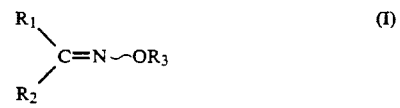

wherein $R_1$ represents an aryl group, an aralkyl group or an alkyl group and $R_2$ and $R_3$ each represents an aralkyl group or an alkyl group, with a proviso that $R_1$ and $R_2$ are not identical.

8 Claims, No Drawings

PROCESS FOR ISOMERIZATION OF OXIME ETHERS

The present invention relates to a process for isomerization of unsymmetrical ketoxime ethers using a specific Lewis acid as an isomerizing agent.

Unsymmetrical ketoxime ethers are compounds which are important as medicines, agricultural chemicals or intermediates thereof. They are also useful starting materials for optically active amines. It is well known that they are produced in the form of a mixture of anti-isomer and syn-isomer. (Japanese Patent Kokai No.62-215558).

However, in many cases, only the anti-isomer or the syn-isomer is necessary as a medicine. An agricultural chemical or intermediate thereof and as a starting material for optically active amines. In such cases, these two isomers must be separated from each other. Furthermore, in such cases, the other isomer is useless.

Therefor, it is an important technique to isomerize unsymmetrical ketoxime ether to increase the content of necessary isomer or to isomerize the useless isomer or to convert it to the necessary isomer.

As such isomerization process, irradiation with light is known [e.g., J. Chem. Soc., Perkin Trans. 1,9,1691 (1986)]. However, this process suffers from the industrial problem of requiring specific reaction equipment provided with medium pressure vapor mercury lamp.

Another known process is to isomerize unsymmetrical aldoximes with boron trifluoride [e.g., J. Org. Chem. 20, 1491 (1955)]. However, when this process is applied to isomerization of unsymmetrical ketoxime ethers, the reaction rate is extremely low and isomerization efficiency is much deteriorated.

The present inventors have conducted an intensive research in an attempt to solve these problems. As a result, they have found that isomerization reaction proceeds very efficiently in the presence of a specific Lewis acid as an isomerizing agent and accordingly, further research has been conducted. Thus, the present invention has been accomplished.

That is, the present invention provides an industrially excellent process for isomerization of unsymmetrical ketoxime ethers, characterized in that at least one Lewis acid selected from titanium chlorides, titanium bromides, aluminum chlorides, aluminum bromides, boron chlorides or boron bromides is used as an isomerizing agent in isomerization of unsymmetrical ketoxime ethers.

The present invention will be explained in detail.

The unsymmetrical ketoxime ethers used in the present invention include for example, anti-isomer and syn-isomer of the compound represented by the following formula (I) or a mixture of thereof:

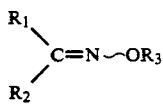
(I)

(wherein $R_1$ represents an aryl group, an aralkyl group or an alkyl group and $R_2$ and $R_3$ each represents an aralkyl group or an alkyl group, with a proviso that $R_1$ and $R_2$ are not identical).

As the substituent $R_1$, mention may be made of, for example, a phenyl group; halogen-substituted phenyl groups such as o-, m- or p-chlorophenyl, o-, m- or p-bromophenyl, and 2,3-, 2,4-, 2,5-, 2,6-, 3,4- or 3,5-dichlorophenyl; alkyl-substituted phenyl groups such as o-, m- or p-methylphenyl, o-, m- or p-ethylphenyl, o-, m- or p-propylphenyl, o-, m- or p-butylphenyl, and 2,3-, 2,4-, 2,5-, 2,6-, 3,4-, or 3,5-dimethylphenyl; alkoxy-substituted phenyl groups such as o-, m- or p-methoxyphenyl, o-, m- or p-ethoxyphenyl and o-, m- or p-propoxyphenyl; benzyloxy-substituted phenyl groups such as o-, m- or p-benzyloxyphenyl, 2-benzyloxy-3-methylphenyl, 2-benzyloxy-4-methylphenyl, 2-benzyloxy-5-methylphenyl, 2-benzyloxy-5-t-butylphenyl, 2-benzyloxy-3-methoxyphenyl, 2-benzyloxy-4-methoxyphenyl, 2-benzyloxy-5-methoxyphenyl, and 2-benzyloxy-3,5-dichlorophenyl; aryl groups such as o-, m- or p-cyanophenyl and α- or β-naphthyl; a benzyl group; alkyl-substituted benzyl groups such as o-, m- or p-tolylmethyl, o-, m- or p-ethylbenzyl, and 2,3-, 2,4-, 2,5-, 2,6-, 3,4-, or 3,5-dimethylbenzyl; alkoxy-substituted benzyl groups such as o-, m- or p-methoxybenzyl, o-, m- or p-ethoxybenzyl, and 2,3-, 2,4-, 2,5-, 2,6-, 3,4- or 3,5-dimethoxybenzyl; alkyl-substituted phenylethyl groups such as 2-phenylethly, 2-(o-, m- or p-tolyl) ethyl, and (2,3-, 2,4-, 2,5-, 2,6-, 3,4-, or 3,5-dimethylphenyl)ethyl; alkoxy-substituted phenylethyl groups such as o-, m- or p-methoxyphenylethyl, o-, m- or p-ethoxyphenylethyl, and 2,3-, 2,4-, 2,5-, 2,6-, 3,4-, or 3,5-dimethoxyphenylethyl; aralkyl groups such as 3-phenylpropyl and naphthylmethyl; and alkyl groups such as methyl, ethyl, propyl, butyl, pentyl and hexyl.

Substituents $R_2$ and $R_3$ include, for example, the same aralkyl groups and alkyl groups as of $R_1$.

As representative examples of unsymmetrical ketoxime ethers, mention may be made of o-methyl, o-octyl, o-cyclohexyl, and o-benzyl oximes of acetophenone, propiophenone, butyrophenone, isobutyrophenone, chloromethyl(phenyl) ketone, bromomethyl(phenyl) ketone, o-methoxyacetophenone, o-ethoxyacetophenone, o-propoxyacetophenone, o-benzyloxyacetophenone, o-chloroacetophenone, m-chloroacetophenone, p-chloroacetophenone, o-bromoacetophenone, m-bromoacetophenone, p-bromoacetophenone, 2',3'-, 2',4'-, 2',5'-, 2',6'-, 3',4'-, or 3',5'-dichloroacetophenone, 2',3'-, 2',4'-, 2',5'-, 2',6'-, 3',4'- or 3',5'-dibromoacetophenone, α-acetonaphthone, β-acetonaphthone, p-cyanoacetophenone, phenylbenzyl ketone, phenyl(o-tolylmethyl) ketone, phenyl(m-tolylmethyl) ketone, phenyl(p-tolylmethyl) ketone, phenyl (2-phenylethyl) ketone, 2-pentanone, 2-hexanone, 2-heptanone, 2-octanone, 3-heptanone, 3-octanone, cyclohexyl methyl ketone, cyclohexyl ethyl ketone, cyclohexyl benzyl ketone, α-phenylacetone, (2-phenylethyl)methyl ketone, (2-phenylethyl)ethyl ketone, and (3-phenylpropyl)methyl ketone. Syn-isomers, anti-isomers thereof and mixtures of them are used.

These ketoxime ethers can be easily produced from the corresponding ketones in accordance with known processes.

The feature of the present invention is to use at least one Lewis acid selected from the group consisting of titanium chloride, titanium bromide, aluminum chloride, aluminum bromide, boron chloride, and boron bromide. Specific examples are titanium tetrachloride, titanium trichloride, titanium tetrabromide, aluminum trichloride, aluminum tribromide, boron trichloride, and boron tribromide. Mixtures of these compounds may also be used.

Amount of the Lewis acid is normally about 0.02-2 mols, preferably about 0.05-1 mol per 1 mol of the ketoxime ether.

Isomerization reaction is usually carried out in the presence of a solvent. The solvent includes, for example, ethers such as dioxane, tetrahydrofuran, and diglyme, hydrocarbons such as benzene, toluene and xylene, halogenated hydrocarbons such as chlorobenzene, chloroform, and 1,2-dichloroethane, and mixed solvents thereof. Amount of the solvent is usually about 2-50 times the weight of ketoxime ether.

Reaction temperature is usually not more than 150° C., preferably −20° −60° C.

Progress of reaction can be confirmed by analysis means such as gas chromatography.

After completion of the reaction, for example, an aqueous solution of sodium hydrogencarbonate or the like is added to reaction mixture to inactivate the isomerizing agent and then the reaction mass is subjected to extraction with an organic solvent such as ether to obtain the desired product from organic layer.

Thus, isomerized unsymmetrical ketoxime ethers are obtained. According to the present invention, isomerization can be allowed to proceed very efficiently even under mild conditions without using special apparatuses. That is, the process of the present invention is advantageous as a process for industrial isomerization of ketoxime ethers.

The present invention will be explained in more detail by the following nonlimiting examples.

EXAMPLE 1

Titanium tetrachloride (0.1 mmol, 19 mg) was added to a solution of syn-phenyl(p-tolylmethyl) ketone (o-methyloxime)(anti/syn=0.7/99.3)(1 mmol, 0.24 g) in tetrahydrofuran (1 ml) at 25° C. in nitrogen atmosphere, followed by stirring for 38 hours at 25° C.

Then, a saturated aqueous sodium hydrogencarbonate solution was added to the reaction mixture and thereafter, the reaction mixture was subjected to extraction with addition of ethyl ether. The resulting organic layer was concentrated to obtain 0.24 g of anti-phenyl(p-tolylmethyl) ketone (o-methyloxime). Anti/syn ratio was measured by gas chromatography. Anti/syn was 97.5/2.5 and yield was 100%.

EXAMPLES 2 and 3

Example 1 was repeated except that toluene or 1,2-dichloroethane was used in place of the tetrahydrofuran as solvent, thereby to obtain anti-phenyl(p-tolylmethyl) ketone (o-methyloxime). The results are shown in Table 1.

TABLE 1

| Example | Solvent | After isometrization anti/syn | Yield (%) | Reaction time (hr) |
|---|---|---|---|---|
| 1 | Toluene | 97.0/3.0 | 99 | 13 |
| 2 | 1,2-Dichloroethane | 96.9/3.1 | 98 | 22 |

EXAMPLES 4-9 and COMPARATIVE EXAMPLE 1

Example 1 was repeated except that anti-syn mixed phenyl(p-tolylmethyl) ketone (o-methyloxime) (anti/syn=63.6/36.4) was used in place of the syn-phenyl (p-tolylmethyl) ketone (o-methyloxime) and 0.1 mmol of titanium trichloride, titanium tetrabromide, boron trichloride, boron tribromide, aluminum trichloride, aluminum tribromide, or boron trifluoride etherate was used in place of the titanium tetrachloride. As a result, the desired products were quantitatively obtained without producing by-products. The results are shown in Table 2.

TABLE 2

| Example | Lewis acid | Anti/syn after isomerization | Reaction time hr |
|---|---|---|---|
| 4 | Titanium trichloride | 97.5/2.5 | 22 |
| 5 | Titanium tetrabromide | 97.4/2.6 | 19 |
| 6 | Boron trichloride | 97.2/2.8 | 109 |
| 7 | Boron tribromide | 96.9/3.1 | 22 |
| 8 | Aluminum trichloride | 96.5/3.5 | 16 |
| 9 | Aluminum tribromide | 97.3/2.7 | 22 |
| Comparative Example | Boron trifluoride | 82.5/17.5 | 264 |

EXAMPLES 10-21

Example 1 was repeated except that phenyl (p-tolylmethyl) ketone (o-butyloxime), phenyl(p-tolylmethyl) ketone (o-benzyloxime), 2-octanone (o-benzyloxime), syn-p-bromoacetophenone (o-methyloxime), syn-2',4'-dichloroacetophenone (o-emthyloxime), anti-2',4'-dichloroacetophenone (o-methyloxime), syn-3',4'-dichloroacetophenone (o-methyloxime), syn-p-chloroacetophenone (o-methyloxime), syn-o-chloroacetophenone (o-methyloxime), syn-o-chloroacetophenone (o-methyloxime), anti-o-chloroacetophenone (o-methyloxime), anti-o-chloroacetophenone (o-methyloxime), syn-o-chloroacetophenone (o-methyloxime), syn-o-methylacetophenone (o-methylacetophenone, or anti-o-methylacetophenone (o-methyloxime) was used in place of the syn-phenyl(p-tolymethyl) ketone (o-methyloxime).

In all cases, no by-product was produced and the desired product was able to be obtained quantitatively. The results are shown in Table 3.

TABLE 3

| Example | Oxime ether | Reaction time (hr) | Anti/Syn Before isometrization ↓ After isometrization |
|---|---|---|---|
| 10 | Phenyl (p-tolylmethyl) ketone (o-butyloxime) | 14 | 83.5/16.5 ↓ 97.8/2.2 |
| 11 | Phenyl (p-tolylmethyl) ketone (o-benzyloxime) | 22 | 63.7/36.3 ↓ 97.7/2.3 |
| 12 | 2-Octanone (o-benzyloxime) | 13 | 0.7/99.3 ↓ 77.1/22.9 |
| 13 | Syn-p-bromoacetophenone (o-methyloxime) | 14 | 0.3/99.7 ↓ 99.2/0.8 |
| 14* | Syn-2', 4'-dichloroacetophenone (o-methyloxime) | 85 | 0.1/99.9 ↓ 83.1/16.9 |
| 15* | Anti-2', 4'-dichloroacetophenone (o-methyloxime) | 85 | 99.8/0.2 ↓ 82.1/17.9 |
| 16 | Syn-3', 4'-dichloroacetophenone (o-methyloxime) | 15 | 0.2/99.8 ↓ 99.3/0.7 |
| 17 | Syn-p-chloroacetophenone (o-methyloxime) | 14 | 0.4/99.6 ↓ 99.3/0.7 |
| 18* | Syn-o-chloroaceto- | 90 | 0.5/99.5 |

TABLE 3-continued

| Example | Oxime ether | Reaction time (hr) | Anti/Syn Before isometrization ↓ After isometrization |
|---|---|---|---|
| | phenone (o-methyl-oxime) | | ↓ 83.4/16.6 |
| 19* | Anti-o-chloroaceto-phenone (o-methyl-oxime) | 90 | 98.6/1.4 ↓ 83.6/16.4 |
| 20 | Syn-o-methylaceto-phenone (o-methyl-oxime) | 83 | 0/100 ↓ 78.8/21.2 |
| 21 | Anti-o-methylaceto-phenone (o-methyl-oxime) | 64 | 100/0 ↓ 79.2/20.8 |

*Titanium tetrachloride was used in an amount of 0.5 mmol.

We claim:

1. A process for isomerization of an unsymmetric ketoxime ether comprising isomerizing an unsymmetric ketoxime ether in the presence of 0.5-1 mol per mol of the unsymmetric ether of at least one Lewis acid isomerizing agent selected from the group consisting of a titanium chloride, a titanium bromide, an aluminum chloride, an aluminum bromide, a boron chloride and a boron bromide.

2. The process according to claim 1, wherein the Lewis acid isomerizing agent is selected from the group consisting of titanium tetrachloride, titanium trichloride, aluminum trichloride, aluminum tribromide, boron trichloride and boron tribromide.

3. The process according to claim 1, wherein the unsymmetric ketoxime ether is an anti-isomer or a syn-isomer of a compound represented by following formula (I):

$$\begin{array}{c} R_1 \\ \phantom{R_1}\diagdown \\ \phantom{R_1R_1}C=N-OR_3 \\ \phantom{R_1}\diagup \\ R_2 \end{array} \quad (I)$$

wherein $R_1$ represents an unsubstituted or substituted aryl group, an unsubstituted or substituted aralkyl group of a lower alkyl group and $R_2$ and $R_3$ each represents an unsubstituted or substituted aralkyl group or a lower alkyl group, with a proviso that $R_1$ and $R_2$ cannot be identical, or a mixture of the anti-isomer compound and the syn-isomer compound.

4. The process according to claim 3, wherein $R_1$ of formula (I) is phenyl, cyano-substituted phenyl, halogen-substituted phenyl, lower alkyl-substituted phenyl, lower alkoxy-substituted phenyl, benzyloxy-substituted phenyl, naphthyl, benzyl, lower alkyl-substituted benzyl, lower alkoxy-substituted benzyl, phenylethyl, lower alkyl-substituted phenylethyl, phenylpropyl, naphthylmethyl, methyl, ethyl, propyl, butyl, pentyl or hexyl.

5. The process according to claim 3, wherein $R_2$ of formula (I) is benzyl, lower alkyl-substituted benzyl, lower alkoxy-substituted benzyl, phenylethyl, lower alkyl-substituted phenylethyl, phenylpropyl, naphthylmethyl, methyl, ethyl, propyl, butyl, pentyl or hexyl.

6. The process according to claim 3, wherein $R_3$ of formula (I) is benzyl, lower alkyl-substituted benzyl, lower alkoxy-substituted benzyl, phenylethyl, lower alkyl-substituted phenylethyl, phenylpropyl, naphthylmethyl, methyl, ethyl, propyl, butyl, pentyl, or hexyl.

7. The process according to claim 1, wherein the isomerization temperature is not over 150° C.

8. The process according to claim 1, wherein the isomerization temperature is −20° to 60° C.

* * * * *

UNITED STATES PATENT AND TRADEMARK OFFICE
CERTIFICATE OF CORRECTION

PATENT NO. : 5,130,486
DATED : July 14, 1992
INVENTOR(S) : Naoto Konya et al It is certified that error appears in the above-identified patent and that said Letters Patent is hereby corrected as shown below:

On the title page: Item [75] Inventors: "Naoto Konyo" should read -- Naoto Konya --.

Signed and Sealed this

Twenty-second Day of June, 1993

Attest:

MICHAEL K. KIRK

Attesting Officer

Acting Commissioner of Patents and Trademarks

UNITED STATES PATENT AND TRADEMARK OFFICE
CERTIFICATE OF CORRECTION

PATENT NO. : 5,130,486

DATED : July 14, 1992

INVENTOR(S) : Naoto Konya et al

It is certified that error appears in the above-indentified patent and that said Letters Patent is hereby corrected as shown below:

Column 5, line 21, claim 3, change "0.5-1 mol" to --0.05-1 mol--

Signed and Sealed this

Twenty-third Day of May, 1995

Attest:

Attesting Officer

BRUCE LEHMAN

Commissioner of Patents and Trademarks